(12) United States Patent
Decourcelle et al.

(10) Patent No.: US 8,683,871 B2
(45) Date of Patent: Apr. 1, 2014

(54) PROCESS FOR MANUFACTURING A LAMINATED GLAZING

(75) Inventors: Romain Decourcelle, Compiegne (FR); Fabien Levasseur, Longueil-Annel (FR); Jean-Clement Nugue, Lamorlaye (FR)

(73) Assignee: Saint-Gobain Glass France, Courbevoie (FR)

( * ) Notice: Subject to any disclaimer, the term of this patent is extended or adjusted under 35 U.S.C. 154(b) by 438 days.

(21) Appl. No.: 13/120,311

(22) PCT Filed: Sep. 30, 2009

(86) PCT No.: PCT/FR2009/051860
§ 371 (c)(1),
(2), (4) Date: Mar. 22, 2011

(87) PCT Pub. No.: WO2010/037973
PCT Pub. Date: Apr. 8, 2010

(65) Prior Publication Data
US 2011/0200831 A1 Aug. 18, 2011

(30) Foreign Application Priority Data
Oct. 1, 2008 (FR) .................................. 08 56642

(51) Int. Cl.
*G01B 5/00* (2006.01)
(52) U.S. Cl.
USPC ............................. 73/785; 73/804; 428/426
(58) Field of Classification Search
USPC ............ 73/760, 774, 787, 788, 804; 428/426
See application file for complete search history.

(56) References Cited

U.S. PATENT DOCUMENTS 5,131,967 A * 7/1992 Tweadey et al. .............. 156/101
(Continued)

FOREIGN PATENT DOCUMENTS

| EP | 0 844 075 | 5/1998 |
|---|---|---|
| FR | 2 616 908 | 12/1988 |

(Continued)

OTHER PUBLICATIONS

U.S. Appl. No. 13/381,530, filed Dec. 29, 2011, Nugue, et al.

(Continued)

*Primary Examiner* — Max Noori
(74) *Attorney, Agent, or Firm* — Oblon, Spivak, McClelland, Maier & Neustadt, L.L.P.

(57) ABSTRACT

A process for manufacturing a laminated glazing, in which a lamination interlayer is interposed between two substrates having a glass function, including: making a measurement of Young's modulus E on a sample of the interlayer, using a viscoanalyzer, by varying temperature and frequency while imposing a constant dynamic displacement; making a numerical treatment of curves obtained, using WLF (Williams-Landel-Ferry) equations, to establish a law E(f) governing behavior of a material constituting the interlayer sample at a given temperature; producing a numerical model based on a finite-element method in bending of a laminated glazing panel, wherein mechanical properties of the sample result from the preceding operations; comparing results of the numerical calculation with those obtained with analytical formulae in which participation of the interlayer in transferring shear in the laminated glazing is represented by a transfer coefficient ω; varying the transfer coefficient ω in the analytical formulae until results converge; and constructing a transfer function ω=f(E) by successive iterations.

8 Claims, 1 Drawing Sheet

(56) References Cited

U.S. PATENT DOCUMENTS

Figure 1:
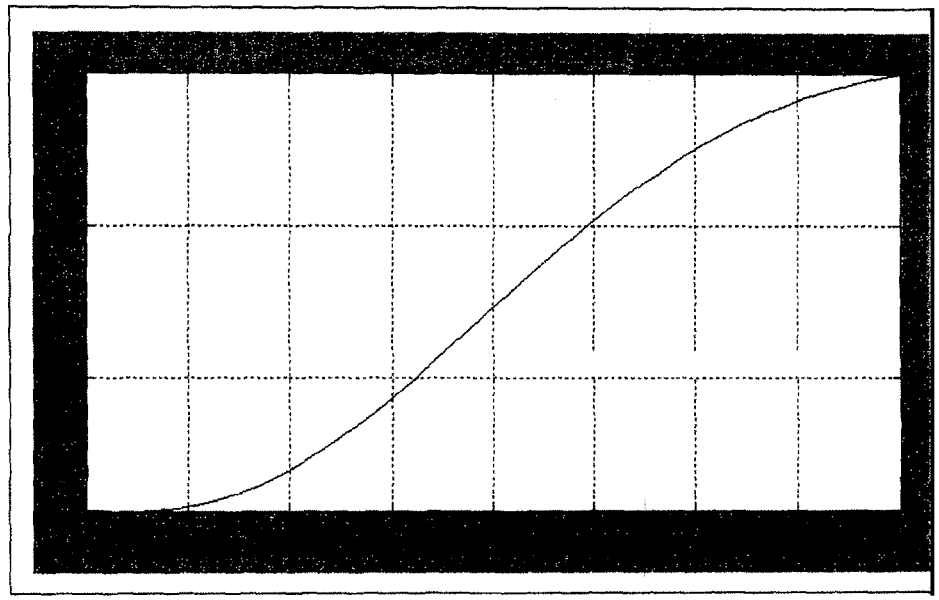

| | | | |
|---|---|---|---|
| 5,540,961 A * | 7/1996 | Reul et al. .................... 428/34 |
| 6,074,732 A | 6/2000 | Garnier et al. |
| 6,156,417 A * | 12/2000 | Edwards et al. ............ 428/215 |
| 6,432,522 B1 | 8/2002 | Friedman et al. |
| 8,389,120 B2 * | 3/2013 | Delatte .................... 428/415 |
| 2002/0006504 A1 * | 1/2002 | Rehfeld et al. ............ 428/212 |
| 2007/0284916 A1 | 12/2007 | Charlier |
| 2009/0159362 A1 | 6/2009 | Boure et al. |
| 2012/0034439 A1 * | 2/2012 | Milamon et al. ............ 428/215 |
| 2012/0135248 A1 * | 5/2012 | Nugue et al. ................ 428/426 |

FOREIGN PATENT DOCUMENTS

| | | |
|---|---|---|
| FR | 2 875 182 | 3/2006 |
| WO | 03 053688 | 7/2003 |
| WO | 2007 135317 | 11/2007 |

OTHER PUBLICATIONS

International Search Report issued Mar. 1, 2010 in PCT/FR09/51860 filed Sep. 30, 2009.

* cited by examiner

PROCESS FOR MANUFACTURING A LAMINATED GLAZING

The present invention relates to a process for manufacturing a laminated glazing which incorporates a lamination interlayer, the shear transfer coefficient of which has been optimized.

According to another aspect, the invention also relates to a laminated glazing that incorporates this type of optimized interlayer.

It is known that the laws governing the viscoelastic behavior of lamination interlayers intended for the manufacture of laminated glazing have an influence on the mechanical behavior of said laminated glazing when it is subjected to a static or quasi-static load.

The combination of the intensity of these loads, the way in which they are distributed, the time for which they are applied and the temperature of application in the various limiting states, that are applied to the glazing, make it possible to determine the structural characteristics (nature, composition, thickness, etc.) of the interlayer to be used in assembling the laminated glazing.

At the present time, the determination of the structural characteristics of the lamination interlayer to be used in the manufacture of a laminated glazing results from an analytical model that takes into account the equivalent thickness $e_q$ of a theoretical glazing without the interlayer, according to the following equation:

$$\left[ e_q = \sqrt[3]{(1-\omega)\left(\sum_{i=1}^{n} e_i^3\right) + \omega\left(\sum_{i=1}^{n} e_i\right)^3} \right],$$

where:

$\omega$ is the transfer coefficient that characterizes the effective participation of the interlayer in transferring shear between the glass components of the laminated assembly, which coefficient is equal to 0 if the interlayer provides no contribution to the mechanical performance of the assembly formed by the laminated glazing or, on the contrary, has a value that tends towards 1 if the interlayer provides a contribution to the mechanical performance of the laminated glazing; and $e_i$ is the thickness of each glass substrate of the glazing.

No value of the transfer coefficient $\omega$ and no method for determining the transfer coefficient $\omega$ are available in the literature.

The limiting case of $\omega=0$ corresponds to an interlayer providing perfect sliding between the layers of the glazing, in which there is no shear stress transfer, whereas the limiting case of $\omega$ tending towards 1 corresponds to full participation of the interlayer in stress transfer.

It is endeavored to determine the transfer coefficient $\omega$ between these limiting cases so as to determine classes of performance for lamination interlayers: namely "flexible" interlayers, that provide only very little or no shear stress transfer, typically acoustic interlayers; "structuring" interlayers, that provide substantial shear stress transfer; and "standard" interlayers, the shear stress transfer capability of which lies between the two ranges defined above.

Laminated glazings using interlayers that are not optimized as regards their factor $\omega$ are therefore not properly designed, possibly leading to mechanical failures in the event of uncontrolled stressing.

The objective of the present invention is therefore to alleviate these drawbacks by proposing a process for manufacturing a laminated glazing that incorporates at least one optimized lamination interlayer.

For this purpose, one subject of the invention is a process for manufacturing a laminated glazing, in which a lamination interlayer is interposed between two substrates having a glass function, such that, beforehand:

a measurement of the Young's modulus E is made on a sample of said interlayer, using a viscoanalyzer, by varying the temperature and the frequency while imposing a constant dynamic displacement;

a numerical treatment of the curves obtained is made, using the WLF (Williams-Landel-Ferry) equations, in order to establish a law governing the behavior of the material constituting said interlayer sample at a given temperature;

a numerical model based on a finite-element method for bending of a laminated glazing panel is produced, wherein the mechanical properties of the sample result from the preceding steps;

the results of the numerical calculation are compared with those obtained with analytical formulae in which the participation of the interlayer in transferring the shear in the laminated glazing is represented by a transfer coefficient $\omega$;

the transfer coefficient $\omega$ is varied in the analytical formulae until the results converge;

a transfer function $\omega=f(E)$, where $\omega$ is the transfer coefficient and E is the Young's modulus of the interlayer, is constructed by successive iterations.

Thanks to this optimized interlayer, the laminated glazing incorporating the latter has improved mechanical properties corresponding to the mechanical stressing to which it is subjected.

Within the context of the invention, a substrate having a glass function may be a glass substrate or a plastic substrate.

In preferred embodiments of the invention, one or both of the following provisions may optionally furthermore be applied:

the temperature is varied between −20° C. and +60° C.;
the frequency is varied between $5 \times 10^{-7}$ Hz and $3 \times 10^{-1}$ Hz.

According to another aspect, another subject of the invention is also a group of interlayers that can be used within a laminated glazing manufactured in this way.

An interlayer is said to have a "structuring" function if, for a wind load time of 3 s and for a use temperature between 0° C. and 20° C.:
at 0° C., $E > 8 \times 10^8$ Pa;
at 10° C., $E > 3 \times 10^8$ Pa;
at 20° C., $E > 1 \times 10^8$ Pa.

An interlayer is said to have a "standard" function if, for a wind load time of 3 s and for a use temperature between 0° C. and 20° C.:
at 0° C., $E > 1 \times 10^8$ Pa and $E \leq 8 \times 10^8$ Pa;
at 10° C., $E > 2 \times 10^7$ Pa and $E \leq 3 \times 10^8$ Pa;
at 20° C., $E > 5 \times 10^6$ Pa and $E \leq 1 \times 10^8$ Pa.

An interlayer is said to have a "flexible or acoustic" function if, for a wind load time of 3 s and for a use temperature between 0° C. and 20° C.:
at 0° C., $E > 1 \times 10^7$ Pa and $E \leq 1 \times 10^8$ Pa;
at 10° C., $E > 3 \times 10^6$ Pa and $E \leq 2 \times 10^7$ Pa;
at 20° C., $E > 5 \times 10^8$ Pa and $E \leq 5 \times 10^6$ Pa.

Another subject of the invention is a laminated glazing comprising at least a first substrate having a glass function and a second substrate having a glass function, these substrates being laminated using an interlayer as described above.

Another subject of the invention is a laminated glazing comprising at least a first substrate having a glass function and a second substrate having a glass function between which a lamination interlayer is interposed, this laminated glazing being manufactured according to a process as described above.

Figure 2:
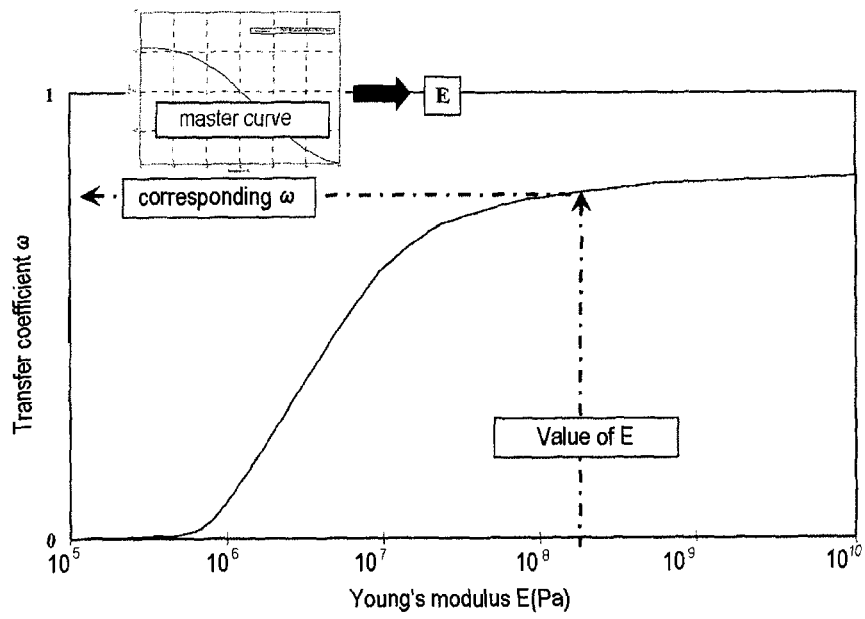

The features and advantages of the invention will become apparent in the following description of a method of carrying out a process for manufacturing a laminated glazing according to the invention, given solely by way of example and with reference to the appended drawings in which:

FIG. 1 shows the master curve at 20° C. for a structuring interlayer, namely the Young's modulus E at 20° C. as a function of the frequency f, which varies from $1\times10^{-7}$ to $1\times10^1$ Hz;

FIG. 2 gives an example of the curve of the transfer function, or transfer curve $\omega = f(E)$, where $\omega$ is the transfer coefficient and E is the Young's modulus of the interlayer.

According to a preferred embodiment of the invention, starting with two substrates having a glass function that are intended to be assembled by a lamination technique using a lamination interlayer, the mechanical parameters of said interlayer are characterized beforehand, using a viscoanalyzer (VA400) sold by the company Metravib.

After a sample of said interlayer has been placed in the above viscoanalyzer, the Young's modulus is measured on the sample of said interlayer using the viscoanalyzer, by varying the temperature and the frequency while imposing a constant dynamic displacement, in particular in this example a displacement of $1\times10^{-6}$ m.

A sample of an interlayer of the "RM11" brand sold by the company Solutia was tested, giving, for a load time of 3 s and at 20° C., a Young's modulus E of $2\times10^8$ Pa.

Next, a numerical treatment of the curves obtained is made using the WLF (Williams-Landel-Ferry) equations (J. D. Ferry, "Viscoelastic Properties of Materials", published by Wiley (1980)) in order to establish the behavior law $E(f)$, i.e. the variation of the Young's modulus E as a function of the frequency, of the material constituting said interlayer sample at a given temperature, this temperature, here 20° C., being generally called the master temperature.

A numerical model based on a finite element method for bending of a panel of the laminated glazing is produced, wherein the mechanical properties of the sample result from the preceding steps. This numerical model can be produced using COSMOS-M computation software, into which a nonlinear model of a laminated glazing plate including the interlayer in question is incorporated, the plate being simply supported on each side, with a uniform load.

The results of the numerical calculation are then compared with those obtained with analytical formulae in which the contribution of the interlayer to shear transfer in the laminated glazing is represented by the transfer coefficient co. Such analytical formulae are the subject of Appendix B of the draft European standard prEN 13474. These analytical formulae involve in particular the thickness of the glazing, which may for example be given by the following equation for the equivalent thickness $e_q$ of the laminated glazing:

$$e_q = \sqrt[3]{(1-\omega)\left(\sum_{i=1}^{n} e_i^3\right) + \omega\left(\sum_{i=1}^{n} e_i\right)^3}$$

in which $e_i$ is the thickness of each substrate having a glass function of the glazing.

The transfer coefficient $\omega$ is varied in the analytical formulae until the results converge, and a transfer function $\omega = f(E)$, an illustrative example of which is given in FIG. 2, is constructed by successive iterations.

From this curve, for this sample, at 20° C. and for a load time of 3 s, a value $\omega = 0.7$ was obtained. Under these conditions, the interlayer may be termed a "structuring" interlayer.

The process according to the invention was repeated with other lamination interlayers and the following were obtained:
   with an interlayer of the RB41 brand sold by Solutia, at 20° C. for a wind load time of 3 s, E=9 MPa, $\omega = 0.4$. Under these conditions, the interlayer may be termed a "standard" interlayer; and
   with an interlayer of the SC brand sold by KEG, at 20° C. for a wind load time of 3 s, E=1 MPa, $\omega = 0.1$. Under these conditions, the interlayer may be termed a "flexible or acoustic" interlayer.

Using an interlayer of each of these types, it is possible to produce laminated glazing comprising two substrates S1 and S2 joined together via one of their main faces using this interlayer.

The invention claimed is:

1. A process for manufacturing a laminated glazing, in which a lamination interlayer is interposed between two substrates having a glass function, the process comprising:
   making a measurement of Young's modulus E on a sample of the interlayer, using a viscoanalyzer, by varying temperature and frequency while imposing a constant dynamic displacement;
   making a numerical treatment of curves obtained, using WLF (Williams-Landel-Ferry) equations, to establish a law governing behavior of a material constituting the interlayer sample at a given temperature;
   producing a numerical model based on a finite-element method in bending of a laminated glazing panel, wherein mechanical properties of the sample result from the preceding operations;
   comparing results of the numerical calculation with those obtained with analytical formulae in which participation of the interlayer in transferring shear in the laminated glazing is represented by a transfer coefficient $\omega$;
   varying the transfer coefficient $\omega$ in the analytical formulae until results converge; and
   constructing a transfer function $\omega = f(E)$, wherein $\omega$ is the transfer coefficient and E is the Young's modulus of the interlayer, by successive iterations.

2. The manufacturing process as claimed in claim 1, wherein the temperature is varied between −20° C. and +60° C.

3. The manufacturing process as claimed in claim 1, wherein the frequency is varied between $5\times10^{-7}$ Hz and $3\times10^{-1}$ Hz.

4. An interlayer used in the process as claimed in claim 1, wherein the interlayer has a structuring function and is such that, for a wind load time of 3 s and for a use temperature between 0° C. and 20° C.:
   at 0° C., $E > 8\times10^8$ Pa;
   at 10° C., $E > 3\times10^8$ Pa;
   at 20° C., $E > 1\times10^8$ Pa.

5. An interlayer used in the process as claimed in claim 1, wherein the interlayer has a standard function and is such that, for a wind load time of 3 s and for a use temperature between 0° C. and 20° C.:
   at 0° C., $E > 1\times10^8$ Pa; and $E \leq 8\times10^8$ Pa;
   at 10° C., $E > 2\times10^7$ Pa and $E \leq 3\times10^8$ Pa;
   at 20° C., $E > 5\times10^6$ Pa; and $E \leq 1\times10^8$ Pa.

6. An interlayer used in the process as claimed in claim 1, wherein the interlayer has a flexible or acoustic function and is such that, for a wind load time of 3 s and for a use temperature between 0° C. and 20° C.:
   at 0° C., $E > 1\times10^7$ Pa; and $E \leq 1\times10^8$ Pa;
   at 10° C., $E > 3\times10^6$ Pa and $E \leq 2\times10^7$ Pa;
   at 20° C., $E > 5\times10^5$ Pa and $E \leq 5\times10^6$ Pa.

7. A laminated glazing comprising:
at least a first substrate having a glass function; and
a second substrate having a glass function,
the substrates being laminated using an interlayer as claimed in claim 4.

8. A laminated glazing comprising:
at least a first substrate having a glass function; and
a second substrate having a glass function between which a lamination interlayer is interposed,
the lamination interlayer manufactured by a manufacturing process as claimed in claim 1.

* * * * *